(12) United States Patent
Van Tassel et al.

(10) Patent No.: US 6,719,778 B1
(45) Date of Patent: *Apr. 13, 2004

(54) METHODS FOR TREATMENT OF ANEURYSMS

(75) Inventors: Robert A. Van Tassel, Excelsior, MN (US); Michael Kasinkas, Plymouth, MN (US)

(73) Assignee: Endovascular Technologies, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/534,786

(22) Filed: Mar. 24, 2000

(51) Int. Cl.[7] ................................................ A61N 5/01
(52) U.S. Cl. .......................... 607/88; 607/89; 607/92; 604/20
(58) Field of Search ................................. 600/476, 478, 600/473; 606/7, 15; 607/88, 89, 92, 93, 94, 91; 604/20

(56) References Cited

U.S. PATENT DOCUMENTS

| 4,799,479 | A | * | 1/1989 | Spears | 606/7 |
|---|---|---|---|---|---|
| 5,116,864 | A | * | 5/1992 | March et al. | 514/455 |
| 5,405,322 | A | | 4/1995 | Lennox et al. | 604/53 |
| 5,462,733 | A | | 10/1995 | Edelson et al. | 424/93.71 |
| 5,514,707 | A | | 5/1996 | Deckelbaum et al. | 514/455 |
| 5,773,609 | A | | 6/1998 | Robinson et al. | 540/145 |
| 5,776,174 | A | | 7/1998 | Van Tassel | 607/89 |
| 5,795,331 | A | * | 8/1998 | Cragg et al. | 604/53 |
| 5,857,998 | A | | 1/1999 | Barry | 604/96 |
| 5,869,462 | A | | 2/1999 | Dzau | 514/44 |
| 5,876,397 | A | | 3/1999 | Edelman et al. | 606/3 |
| 5,921,954 | A | | 7/1999 | Mohr, Jr. et al. | 604/53 |
| 6,048,333 | A | | 4/2000 | Lennox et al. | 604/113 |
| 6,263,236 | B1 | * | 7/2001 | Kasinkas et al. | 604/21 |
| 6,463,317 | B1 | * | 10/2002 | Kucharczyk et al. | 600/411 |
| 2002/0045848 | A1 | * | 4/2002 | Jaafar et al. | 604/20 |

FOREIGN PATENT DOCUMENTS

WO          9956783          11/1999

OTHER PUBLICATIONS

Grant, W.E. et al., "The Effect of Photodynamic Therapy on the Mechanical Integrity of Normal Rabbit Carotid Arteries," *Laryngoscope*, vol. 105, 867–71 (Aug. 1995).

Perree, J. et al., "Psoralen and Long Wavenlength Ultraviolet Radiation as an Adjuvant Therapy for Prevention of Intimal Hyperplasia and Constrictive Remodeling After Balloon Dilation: A Study in the Rabbit Iliac Artery," *Lasers in Surgery and Medicine*, vol. 23, 281–90 (1998).

* cited by examiner

*Primary Examiner*—Roy D. Gibson
(74) *Attorney, Agent, or Firm*—Fulwider Patton Lee & Utecht, LLP

(57) ABSTRACT

Fibrosis, in at least one layer of a vessel wall, can be used to strengthen a vessel wall. Fibrosis can be induced by irradiating a vessel wall with an energy source, or by inducing injury to the vessel wall. In addition to an energy source, photoactivatable agents can also be used such that the energy activates the photoactivatable agent to cause a thickening of the vessel wall. For example, ultra-violet radiation can be used alone or in conjunction with a photoactivatable agent, such as a psoralen compound, to increase the adventitial volume of a blood vessel. Upon exposure to radiation, preferably ultra-violet A radiation, the photoactivatable agent becomes activated and causes compositional and/or structural changes in the adventitia. The invention provides a method of treating aneurysms by thickening the adventitial layer of the vessel wall at the site of the aneurysm.

50 Claims, 1 Drawing Sheet

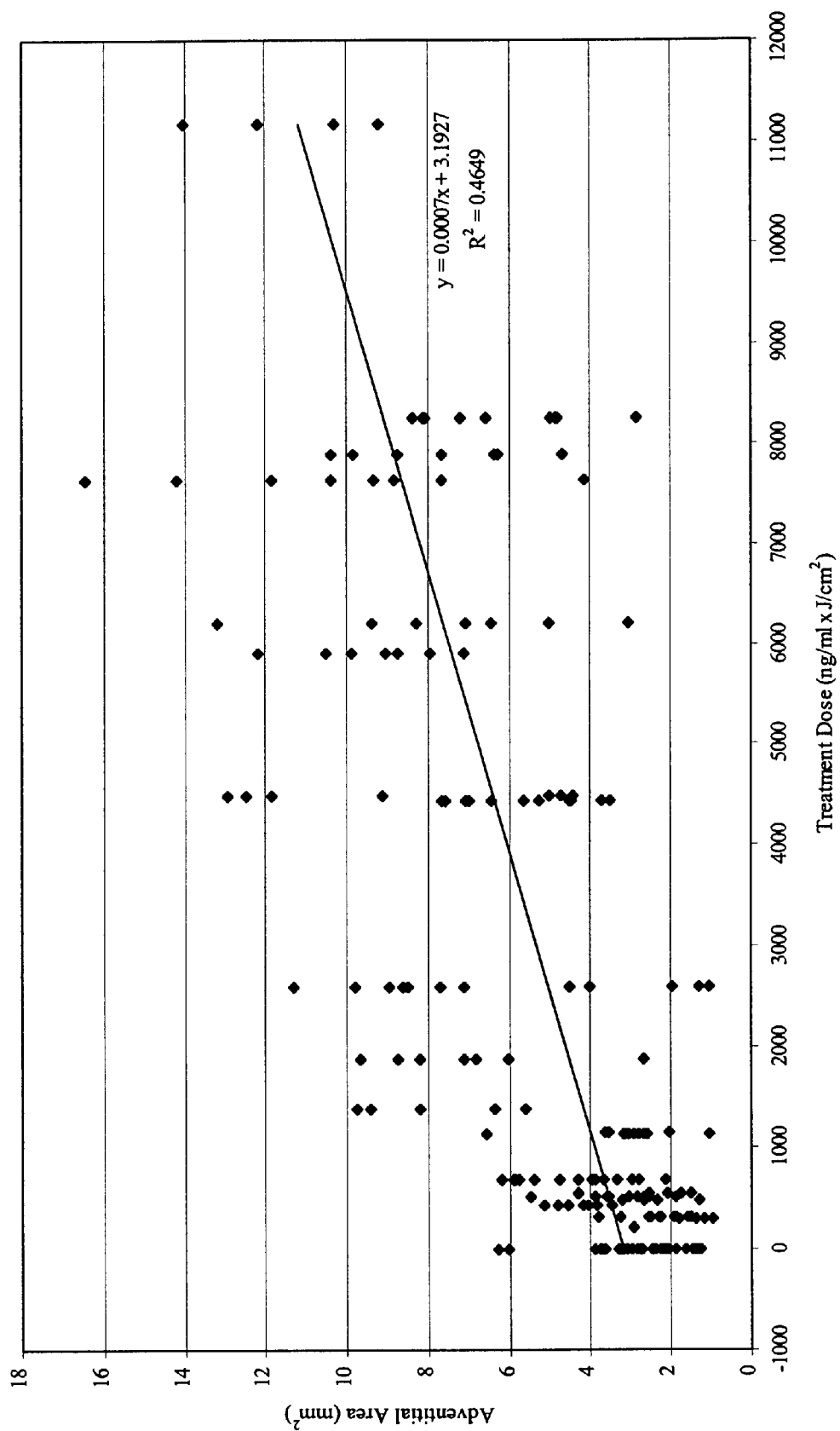
Figure 1: Effect of PUVA Therapy on Adventitial Area

METHODS FOR TREATMENT OF ANEURYSMS

BACKGROUND OF THE INVENTION

The invention relates to a method for strengthening a vessel wall e.g., by irradiation with an energy source, or by inducing injury to the vessel wall, such that the injury initiates a cascade of events leading to fibrosis and a thickening of the vessel wall. In addition to an energy source, a photoactivable agent can also be used such that the energy activates the photoactivable agent which causes structural changes in the vessel wall. More specifically, the invention relates to treating aneurysms using UV radiation with a psoralen compound.

There are two basic types of blood vessels, arteries and veins, which can be distinguished by their structural components. Arteries and veins both have several distinct layers which are arranged coaxially. In arteries, the layers include an inner coat or endothelial layer (intima), an internal elastic lamina, a middle layer (media), and an outer layer (adventitia). Like arteries, veins include an inner layer (intima), a middle layer (media) and an outer layer (adventitia), but the layers are not as thick as in arteries, and provide less structural rigidity.

Both arteries and veins are elastic, and are capable of limited deformation in response to pressure changes. When a diseased blood vessel is exposed to hypertension, dilation may occur at various localized regions. Typically these dilatations are produced at the region in the vessel wall which is weakest, whether inherently or as a result of disease or trauma. As the dilatation progresses, a more pronounced widening or sac, called an aneurysm, is produced, which may burst. A large aneurysm can form clots secondary to a reduction in blood flow in the aneurysmal sac. These clots may emobilize and block distal arteries.

Arteriosclerosis and cystic medial necrosis are two common causes of aneurysms of the thoracic and abdominal aorta. Thoracic aneurysms commonly compress and impact surrounding body structures as they expand. They may impact into the lungs, the spinal column, or the gastrointestinal tract.

Berry aneurysms are congenital defects which occur in cerebral arteries, most commonly at the junctions of vessels in the circle of Willis. These aneurysms appear to be related to defects in the muscular coat of the vessels. Rupture is common, resulting in intracranial hemorrhage.

Other aneurysms include aortic aneurysms, especially abdominal aortic aneurysms (AAA), which are characterized by transmural aortic wall degeneration leading to dilatation, progressive growth, and eventual rupture.

Treatment of aneurysms typically involves either surgical intervention, such as in thoracic or abdominal aneurysms, or coil ablation, such as in aneurysms of the brain. Excision of the aneurysm, and anastomosis of the vessel may be performed, often using a replacement vessel or an artificial prosthesis. Alternatively, a supporting structure such as a stent or other intravascular device may be implanted into the vessel to relieve stress. Examples of stents, include those disclosed in U.S. Pat. No. 4,655,771 issued to Wallsten et al. With the stent positioned at the treatment site, the stent can be radially expanded into a conforming surface in contact with a blood vessel wall. The stents may also be covered with a film or a sheath such as, polytetrafluoroethylene (PTFE) as described in U.S. Pat. No. 5,788,626 to Thompson, et al.

Prostheses used to treat aneurysms are also described in, for example, U.S. Pat. No. 4,681,110 issued to Wiktor et al. Wiktor et al. discloses a flexible tubular liner that is inserted into the aorta to treat aortic aneurysms. The liner has flexible plastic strands designed to elastically expand against the aneurysm and to direct blood flow past the aneurysm.

While these methods achieve the general goal of reducing fatality, these methods have a drawback in that the aneurysm remains a weak area in the blood vessel wall. Mohr et al. in U.S. Pat. No. 5,921,954 describe treating aneurysms using hardening and softening agents, (e.g. collagen), which are applied at the site of the aneurysm. A radio frequency energy is then used to harden the agent and cover the weak region of the blood vessel wall.

Prophylactic methods are used to prevent the formation of aneurysms and rely on reducing the blood pressure, in an effort to reduce mechanical stress on the vasculature. These methods involve using drugs which can have undesirable side effects, e.g., cause kidney or liver damage.

Drugs, such as tetracyclines have been used to prevent abnormal vascular dilation, as described in U.S. Pat. No. 5,834,449 issued to Thompson et al. The tetracycline compounds protect the elastic fibers of the media by selectively inhibiting the elastolytic activity in this region thereby preventing its expansion.

While these methods are effective in treating aneurysms, these methods do not improve the overall structure of the blood vessel which still remains weak at the site of the aneurysm and may still be susceptible to rupture. Accordingly, one purpose of this invention is to provide a method of strengthening a blood vessel.

SUMMARY OF THE INVENTION

The invention pertains to methods for strengthening a vessel wall of a subject by thickening or increasing the strength of at least one layer of the blood vessel wall by inducing fibrosis. Strengthening a vessel wall may be accomplished by either applying energy alone, or by applying energy with agents, such as compounds and therapeutic agents that induce fibrosis. It has been discovered that certain photoactive compounds, such as psoralen agents play a role in regulating the cell proliferation in the adventitial layer of the blood vessel. This invention is based at least, in part, on the surprising discovery that blood vessel walls treated with a psoralen agent, such as 8-methoxypsoralen, (8-MOP) (available commercially as Uvadex, an injectable formulation from Johnson & Johnson, Exton, Penn.), and subsequently irradiated with light, e.g., ultra-violet A (UVA) irradiation, will exhibit fibrosis, especially in the adventitial layer.

The vessel wall can be strengthened by altering the cellular and molecular processes to thicken one or more layers of the vessel wall, for example, by inducing fibrosis in the adventitia of a blood vessel, thereby enabling it to return to a more normal, less weakened state. The method of the invention can be used to treat aneurysms by inducing the fibrosis in the adventitial layer of a blood vessel.

Accordingly, in one aspect, the invention pertains to a method for strengthening the vessel wall of a subject by identifying a region of weakness in a vessel wall, the region of weakness comprising at least one target layer; and applying energy to the region of weakness in an amount effective to induce fibrosis in a target layer, to thereby strengthen the vessel wall. The region of weakness can be identified using techniques such as ultrasound analysis, X-ray analysis, computerized tomography, magnetic resonance imaging (MRI), or angiography.

Energy can be applied to the region of weakness by irradiating the region of weakness with X-ray irradiation in an amount effective to induce fibrosis in a target layer.

Other forms of energy applied in an amount effective to induce fibrosis in a target layer also include, but not limited to, UV irradiation, IR irradiation, microwave irradiation, heat irradiation and RF irradiation.

The method can further comprise, administering a therapeutically effective amount of an agent to a subject, such that the agent is taken up by at least one target layer of the vessel wall. In one embodiment, the agent can be a photoactivatable agent, such that the photoactivatable agent is activated upon irradiation to induce fibrosis in a target layer.

In another aspect, the invention pertains to a method for strengthening a vessel wall of a subject by administering a therapeutically effective amount of a photoactivatable agent to a subject, such that the agent is taken up by at least one layer of the vessel wall, and irradiating a target region of the vessel wall, such that the photoactivatable agent is activated to strengthen the vessel wall.

The photoactivatable agent can be administered using any known methods for administrating therapeutic agents, for example, systemic, local, oral administration, and the like. In one embodiment, the administering step comprises systemically administering the photoactivatable agent. In another embodiment, the administering step comprises locally administering the photoactivatable agent.

The photoactivatable agent can be any agent that is activated by light energy. In the activated state, the photoactivatable agent is capable of causing changes in the cellular and molecular processes in the localized microenvironment, e.g., structural changes by altering cell proliferation in at least one layer of the vessel resulting in a change of thickness in the layer. In one embodiment, the photoactivatable agent is a psoralen agent or a derivative thereof.

The photoactivatable agent can be activated using a light source in a variety of ways. Photoactivation can occur by irradiating a target region internally by a light source applied at the target region in-vivo. Photoactivation may also occur by irradiating the target region using an external light source. The entire area of the subject can be irradiated externally or, a desired localized area can be irradiated externally. In one embodiment, the irradiating step comprises irradiating the target region internally using a light delivery catheter. In another embodiment, the irradiating step comprises irradiating the target region using a light delivery catheter without occluding fluid flow. In yet another embodiment, the irradiating step comprises irradiating the target region externally using an external light delivery source. In a preferred embodiment, the irradiating step comprises irradiating the target region with UV light, preferably with light having a wavelength of about 240 to 370 nanometers. In another embodiment, the irradiating step comprises irradiating the target region to increase the area of the vessel wall outer layer, e.g., the adventitia.

In another aspect, the invention pertains to a method for increasing the adventitial mass of a blood vessel wall within a target region by administering a therapeutically effective amount of a photoactivatable agent to a subject, such that the agent is taken up by the adventitial layer, and irradiating a target region of the blood vessel wall so that the photoactivatable agent is activated to increase the adventitial volume.

In another aspect, the invention pertains to a method for treating an aneurysm by increasing the adventitial volume of a blood vessel by administering a therapeutically effective amount of a photoactivatable agent to a subject, such that the agent is taken up by the adventitial region of the blood vessel, and irradiating the site of the aneurysm so that the photoactivatable agent increases the adventitial volume.

Strengthening a vessel wall of a subject by increasing the volume of at least one layer of the blood vessel wall may also be attained by irradiating the target region with light energy of a specific wavelength. The irradiation alone can be sufficient to activate cellular and molecular process that result in an increase in a vessel wall layer.

Accordingly, in another aspect, the invention pertains to a method for strengthening a vessel wall of a subject by irradiating a target region with UVC irradiation, so that the UVC irradiation induces a structural change in at least one layer of the vessel wall. Additionally, the invention pertains to a method for increasing the adventitial volume of a blood vessel wall by irradiating the target region with UVC irradiation, and more specifically, to a method for treating an aneurysm by increasing the adventitial volume of a blood vessel by irradiating the site of the aneurysm with UVC irradiation.

BRIEF DESCRIPTION OF THE DRAWINGS

FIG. 1 is a graph showing the effect of Psoralen-Ultra Violet A (PUVA) therapy on the adventitial area of a blood vessel.

DETAILED DESCRIPTION

The present invention pertains to methods for strengthening a vessel wall of a subject by identifying a region of possible or actual weakness in the vessel wall, the region of weakness comprising at least one target layer; and applying energy to region of weakness in an amount effective to induce fibrosis in a target layer, to thereby strengthen the vessel wall.

The present invention also pertains to methods for strengthening a vessel wall of a subject by administering a therapeutically effective amount of a photoactivatable agent to the subject, such that the agent is taken up by at least one layer of the vessel wall, and irradiating a target region of the vessel wall, such that the photoactivatable agent is activated to strengthen the vessel wall. The data described herein demonstrates that a psoralen compound (e.g., 8-MOP, available as Uvadex, from Johnson and Johnson) and UVA irradiation causes proliferation of the adventitial layer of a blood vessel. These results are unexpected since psoralen compounds in general have little or no effect on proliferation of cells in the intima or adventitia of a blood vessel.

So that the invention may more readily be understood, certain terms are first defined.

The term "strengthening" as used herein refers to restoring the vessel wall to a more normal, less weakened state in a subject. Strengthening may occur by altering cellular and molecular processes to thicken one or more layers in the vessel wall. Induction of fibrosis may lead to strengthening of a vessel wall. For example, a vessel with an aneurysm is detrimental to the subject because the vessel wall comprising the aneurysm becomes thin and weak, presenting the risk of rupture or dissection. Strengthening the vessel wall involves increasing the area of the vessel wall surrounding the aneurysm so that it becomes thicker and less susceptible to rupture.

The phrase "region of weakness" as used herein refers to an area in a vessel wall that requires strengthening, including, for example, blood vessel regions that are dilated or otherwise deviated in size or shape from a normal or reference value as well as regions that are identified by MRI scanning or other imaging modality.

The phrase "target layer" as used herein refers to at least one layer of a vessel wall in which cellular and molecular processes, such as fibrosis, occur.

The term "energy" as used herein refers to any source from the electromagnetic spectrum that is applied for a duration, and an intensity to cause the desired result. Examples of different forms of energy include but are not limited to X-rays, microwaves, UV radiation, IR radiation, visible light, and radio frequency waves. Energy can also be applied by extracting heat, e.g., with a cryogenic catheter. The phrase "amount effective to induce" as used herein refers to the duration and dosage of energy sufficient to initiate a cascade of events leading to fibrosis.

The term "fibrosis" as used herein refers to the art recognized meaning of the term. Fibrosis is a complex process involving different cell types such as fibroblasts, myofibroblasts, macrophages. Fibrosis is a response to injury in which new extracellular matrix is laid down producing dense amounts of collagen required for wound healing. The cascade of events in wound healing involves activation or release of molecules such as cytokines, growth factors and adhesion molecules. The extracellular matrix growth factors TGFβ, platelet derived growth factor (PDGF), and basic fibroblast growth factor (bFGF) appear to initiate and sustain fibrosis. In particular, TGFβ stimulates collagen and fibronectin formation, suppresses collagenase and induces production of collagenase inhibitors. Wound healing occurs immediately after injury and provides a means to remove the damaged tissue from the wound. Soon after, fibroblasts from the surrounding tissue move into the area of tissue injury leading to an increase in fibroblast and cellularity at the site of injury. The fibroblasts proliferate in the injured area and actively produce macromolecular compounds such as collagen and proteoglycans which are secreted into the extracellular matrix of the target layer. The newly synthesized collagen fibrils are cross-linked by lysyl oxidase and provide structural integrity to the wound. At a final stage, the remodeling stage, the previous randomly organized collagen fibrils are aligned in the direction of mechanical tension and become more organized to increase the mechanical strength of the wounded area. Fibrosis can be induced by physical (e.g., heat, cold) and/or chemical (e.g., sodium hydroxide, hydrogen peroxide) stimuli.

The phrase "therapeutically effective amount" as used herein refers to an amount effective, at dosages and for periods of time necessary, to achieve the desired result. A therapeutically effective amount of the photoactivatable agent or derivatives thereof may vary according to factors such as the disease state, age, and weight of the subject, and the ability of the photoactivatable agent or derivatives thereof (alone or in combination with one or more other agents) to elicit a desired response in the subject. Dosage regimens may be adjusted to provide the optimum therapeutic response. A therapeutically effective amount is also one in which any toxic or detrimental effects of the photoactivatable agent or derivatives thereof are outweighed by the therapeutically beneficial effects.

The phrase "photoactivatable agent" as used herein refers to a material which becomes activated by light energy. In the activated state, the photoactivatable agent is capable of causing changes in the cellular and molecular processes in the localized microenvironment, e.g., structural changes in the tissue layer, such as, altering cell proliferation in the adventitial layer that results in an increase of area in this layer. In one embodiment, the photoactivatable agent is a chromophore. Suitable chromophores are generally selected for absorption of light that is deliverable from common radiation sources (e.g. UV light ranging from 240–370 nm). Examples of chromophores which are photoresponsive to such wavelengths include, but are not limited to, acridines, nitroaromatics and arylsulfonamides. One preferred class of chromophores comprises psoralen compounds.

The phrase "target region" as used herein refers to an area of the vessel wall in need of treatment. When the target area is irradiated by an energy source, it undergoes a compositional or structural change that corrects the defect. The target region is capable of undergoing such changes when irradiated with an energy source alone or in combination with a photoactivatable agent.

Various aspects of the invention are described in more detail in the following subsections:

I. Identification of Regions of Weakness

Standard procedures for identifying regions of weakness in a vessel wall can be employed. For example, visualization using CT scans, X-ray analysis, ultrasound analysis, Magnetic Resonance Imaging (MRI), and computed tomography scans. Having identified the location of the region of weakness, appropriate procedures can be undertaken to treat the region of weakness by inducing fibrosis. Appropriate procedures can include, for example, inserting a catheter at the region of weakness (e.g., an aneurysm), and transmitting a source of energy that induces fibrosis.

The method of the invention also permits early intervention and treatment of regions of weakness. Aneurysms, for example, can be treated by strengthening the vessel wall as soon as the aneurysm has been identified. Typically, the recommended procedure for treating aneurysms involves surgery or applications of stents. Before these procedures are undertaken, the patient is usually monitored until the aneurysm is of a size suitable for treatment. By strengthening the vessel wall as soon as the aneurysm is identified, the risk associated with rupture, embolisms or dissection of the aneurysm is reduced.

II. Injury Induction

Application of a stimuli that results in tissue injury produces a cascade of events that promotes repair of the damaged tissue. A therapeutic method has been developed in which the response to injury is used to strengthen a vessel wall (e.g., blood vessel wall). The cascade of events involves activation and release of molecules such as cytokines, growth factors and adhesion molecules. In particular, fibrosis is a response to tissue injury in which new extracellular medium is laid down producing dense amounts of collagen. Stimuli that causes injury can be used to induce activation of the cascade. The stimuli may be from any range of the electromagnetic spectrum (e.g., heat, light, sound, microwaves, radio frequency waves, or irradiation, (X-ray, UV, IR)) which can be applied using standard means. Stimuli that causes injury can also be chemical such as hydrogen peroxide, sodium hydroxide, and the like, or pressure related, for example, pressure on a vessel wall due to procedures like angioplasty.

In one embodiment, exposure of the vessel wall to heat results in injury to the vessel wall. Heat can be applied over a temperature range of about 40° C. to about 60° C., preferably about 40° C. to about 50° C., and most preferably about 42° C. to about 45° C. for a period of time that results in injury (e.g., 1 minute, 30 seconds, 2 minutes) to a vessel wall. Heat can be applied by direct contact of the vessel wall with the heat source, for example, a device such as a catheter containing a thermocouple. In some cases localized heating may be achieved using a laser, infra-red, or microwave irradiation. The heating conditions should be sufficient to elevate the temperature of the localized area to at least about 42° C. for a period of time that results in injury without killing the cells in the vessel wall.

In another embodiment, cryotherapy techniques may also be used to reduce the temperature of the vessel wall to induce injury. Methods for reducing the temperature of a vessel wall are known in the art (See e.g., U.S. Pat. No. 5,902,299.) The temperature of the vessel can be reduced to cause injury using a catheter that delivers a medium, such as gas, fluid or a mixture thereof at a very low temperature between 14° C. and about −10° C. to the vessel wall.

In another embodiment, exposure of the vessel wall to chemicals can cause injury. Chemical inducers, such as hydrogen peroxide, (Canrgeon et al. (1997) *Exp. Cell. Res.*, 20: 30–37) transition metals such as copper, zinc, cadmium (See e.g., Levinson et al. (1980) *Biochem. Phys. Acta.*, 606: 170–180) can be applied to the vessel wall at concentrations sufficient to cause injury without killing the cells.

In addition to treating arteries, the method of the invention can also be used for other applications for example, treating veins, ureters, urethra, bronchi, biliary, pancreatic duct systems, the gut, eustatian, spermatic and fallopian tubes. The method of the invention may be used to treat an lesion in hollow vessels composed of several tissue layers.

The method of the invention can also be used prophylactically, to prevent the growth of aneurysms, or to induce a reduction in the size of the aneurysm. In, the embodiments, the method of the invention can also be used to inhibit or reduce inflammation in the vessel.

III. Agents

The present invention can be practiced in conjunction with the administration of photoactivatable agents that enhance the effects of irradiation. Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light. (See e.g., Cimino et al. (1985) *Ann. Rev. Biochem.* 54:1151–1193 and Hearst et al. (1984) *Quart. Rev. Biophys.* 17:1–44). Psoralens are a group of compounds that exhibit photoactivation. (See e.g., Parrish et al. (1974) *N. Engl. J. Med,* 291: 1207–1211 and Edelson et al. (1987) *N. Engl. J. Med.,* 316: 297–303), herein incorporated by reference, for detailed descriptions of psoralen compounds. Psoralens and furocoumarins (furanes fused to coumarin and derivatives thereof) are a preferred class of photoactivatable agents. A psoralen compound can be administered to the subject prior to irradiating the target region. The psoralen compound will be preferentially absorbed by the layers of the vessel wall, thus rendering them more susceptible to the UV light.

The interactions of psoralen compounds with DNA have previously been described (See e.g., Malane, et al. (1991) *Ann. N.Y. Acad. Sci.* 636:196–208 also incorporated herein by reference). If a psoralen compound is administered orally, the psoralen compound is absorbed from the digestive tract, reaching peak levels in the blood and other tissues in one to four hours. Psoralen compounds are excreted within 24 hours following oral administration. The psoralen compound is inert prior to exposure to ultraviolet or visible light irradiation and is transiently activated into an excited state following irradiation. The transiently activated compound is capable of photomodifying biological molecules (e.g., DNA, protein) and generating other reactive species, (e.g., singlet oxygen), which are capable of modifying other cellular components.

One type of radiation useful for photoactivation of psoralen compounds is ultraviolet A irradiation. Alternatively, visible light having a wavelength greater than about 420 nm can be useful with certain psoralen compounds (See Gasparro, et al., (1993), 57:1007–1010 herein incorporated by reference).

Without being limited to any particular mechanism or explanation, it is believed that the DNA cross-linking by psoralen compounds proceeds by a two step process. Following administration of the psoralen compound into the subject, the psoralen compound first intercalates within the double helix of intracellular DNA or RNA. Following intercalation, the psoralen compound is covalently added to the polynucleic acid by light energy within the absorption band of the psoralen compound. Either psoralen-RNA or psoralen-DNA monoadducts or cross-links are created upon illumination of the intercalated species. By forming covalent cross-links with base-pair structures, psoralen compounds alter the metabolic activity of a cell (See e.g., Cimino, et al. (1985), *Ann. Rev. Biochem.,* 54:1154–93 also herein incorporated by reference).

Examples of photoactivatable agents useful in the present invention can include, but are not limited to, 5-methoxypsoralen (5-MOP), 8-methoxypsoralen (8-MOP), 4,5',8-trimethylpsoralen (TMP), 4'-aminomethyl-4,5',8-trimethylpsoralen (AMT), 5-chloromethyl-8-methoxypsoralen (HMT), angelicin (isopsoralen), 5-methylangelicin (5-MIP), 3-carboxypsoralen, porphyrin, haematoporphyrin derivative (HPD), photofrin II, benzoporphyrin derivative (BPD), protoporphyrin IX (PpIX), dye haematoporphyrin ether (DHE), polyhaematoporphyrin esters (PHE), 13,17-N,N,N-dimethylethylethanolamine ester of protoporphyrin (PH1008), tetra(3-hydroxyphenyl)-porphyrin (3-THPP), tetraphenylporphyrin monosulfonate (TPPS1), tetraphenylporphyrin disulfonate (TPPS2a), dihaematoporphyrin ether, mesotetraphenylporphyrin, mesotetra(4N-methylpyridyl)prophyrin (T4MpyP), octa-(4-tert-butylphenyl)tetrapyrazinoporphyrazine (OPTP), phthalocyanine, tetra-(4-tert-butyl)phthalocyanine ($t_4$-PcH$_2$), tetra-(4-tert-butyl)phthalocyanatomagnesium ($t_4$-PcMg), chloroaluminum sulfonated phthalocyanine (CASPc), chloroaluminum phthalocyanine tetrasulfate (AlPcTS), mono-sulfonated aluminum phthalocyanine (AlSPc), di-sulfonated aluminum phthalocyanine (AlS2Pc), tri-sulfonated aluminum phthalocyanine (AlS3Pc), tetra-sulfonated aluminum phthalocyanine (AlS4Pc), silicon phthalocyanine (SiPc IV), zinc II phthalocyanine (ZnPc), pyrene, bis(di-isobutyl octadecylsiloxy) silicon 2,3-naphthalocyanine (isoBOSINC), germanium IV octabutoxyphthalocyanine (GePc), rhodamine 101 (Rh-101), rhodamine 110 (Rh-110), rhodamine 123 (Rh-123), rhodamine 19 (Rh-19), rhodamine 560 (Rh-560), rhodamine 575 (Rh-575), rhodamine 590 (Rh-590), rhodamine 610 (Rh-610), rhodamine 640 (Rh-640), rhodamine 6G (Rh-6G), rhodamine 700 (Rh-700), rhodamine 800 (Rh-800), rhodamine B (Rh-B), sulforhodamine 101, sulforhodamine 640, sulforhodamine B, coumarin 1, coumarin 2, coumarin 4, coumarin 6, coumarin 6H, coumarin 7, coumarin 30, coumarin 47, coumarin 102, coumarin 106, coumarin 120, coumarin 151, coumarin 152, coumarin 152A, coumarin 153, coumarin 311, coumarin 307, coumarin 314, coumarin 334, coumarin 337, coumarin 343, coumarin 440, coumarin 450, coumarin 456, coumarin 460, coumarin 461, coumarin 466, coumarin 478, coumarin 480, coumarin 481, coumarin 485, coumarin 490, coumarin 500, coumarin 503, coumarin 504, coumarin 510, coumarin 515, coumarin 519, coumarin 521, coumarin 522, coumarin 523, coumarin 535, coumarin 540, coumarin 540A, coumarin 548, 5-ethylamino-9-diethylaminobenzo α-phenoxazimium (EtNBA), 5-ethylamino-9-di ethyl-aminobenzo α-phenoxazinium (EtNBS), 5-ethylamino-9-diethylaminobenzo α-pheno-selenazinium (EtNBSe), chlorpromazine, chlorpormazine derivatives, chlorophyll derivatives, bacteriochlorophyll derivatives, metal-ligand complexes, tris(2,2'-bipyridine)ruthenium (II) dichloride (RuBPY), tris(2,2'-bipyridine)rhodium (II) dichloride (RhBPY), tris(2,2'-bipyridine)platinum (II) dichloride (PtBPY), pheophorbide, merocyanine 540, vitamin D, 5-amino-laevulinic acid, photosan, chlorin e6, chlorin e6 ethylene-diamide, mono-L-aspartyl chlorin e6, and phenoxazine Nile blue derivatives, stilbene, stilbene derivatives, and 4-(N-2(2-hydroxyethyl)-N-methyl)-aminophenyl)4'-(6-hydroxyhexylsulfonyl)-stilbene (APSS). In a preferred embodiment, the photoactivatable agent is a psoralen.

IV. Administration of Agents

Suitable agents such as photoactivatable agents, may be administered using any known method. Administration may involve needle injections into cells, tissues and fluid spaces or blood vessels. Examples of administering photoactivatable agents include but are not limited to intravenous, intramuscular, aerosol, oral, topical, systemic, ocular, intraperitoneal and/or intrathecal.

In one embodiment, the photoactivatable agent can be administered systemically. Systemically administered photoactivatable agents e.g. psoralen compounds, penetrate the nuclear membrane of cells and can intercalate with the nuclear DNA in target tissue cells. Following intercalation with the target tissue's nuclear DNA, the psoralen compound is photoactivated with ultraviolet light or short wavelength visible light. (See, e.g., Gasparro, et al. (1993), *Photochem. Photobiol.* 57:1007–1010.)

In another embodiment, the photoactivatable agent can be administered locally. Typically, local administration of the agent is achieved through conventional devices such as catheters, laparoscopes, endoscopes, cannulae, direct injection. Approaches for local, intravascular, site-specific administration of agents have also included direct deposition of such agents into the vessel wall through an intravascular delivery system. These intravascular delivery systems generally employ balloon catheters which are easily guided through blood vessels to a region in need of treatment and can then be inflated to fully contact and dilate the entire surrounding vessel wall. A therapeutic agent can then be delivered to the surrounding vessel wall, for example, by diffusion through the balloon or by hydrostatic pressure, as occurs when using a porous balloon catheter.

Other balloon catheters which have been used for drug delivery to blood vessel walls are drug-coated catheters (e.g., hydrogel catheters). Upon inflation of the balloon in a blood vessel, the therapeutic agent is "pressed" onto or into the surrounding vessel wall. (See, e.g., Sheriff, et al., (1993), *J. Am. Coll. Cardiol.* 21:188A herein incorporated by reference). Typically, the balloon must be chaperoned by a protective sheath as the catheter is advanced toward the target vessel.

In a preferred embodiment, a non-occluding catheter can be used. Non-occluding catheters are described in a co-pending application by Kasinkas et al. entitled "Non-Occluding Light Delivery Catheter" and is incorporated herein by reference. The non-occluding catheter is designed to deliver the agent to the target region in the vessel wall while permitting blood flow through the vessel wall.

V. Activation of Photoactivatable Agents

Photoactivatable agents can be activated using a monochromatic light source such as a laser. In one embodiment, the photoactivatable agent is activated internally. For example, the light output may be coupled to an invasive, light delivery catheter for conduction and delivery to a remote target region. Such interventional light delivery catheters are well known in the art and are described, for example, in U.S. Pat. No. 5,169,395 issued to Narisco, et al., U.S. Pat. No. 5,196,005 issued to Doiron, et al., U.S. Pat. No. 4,773,999 issued to Spear, et al. and U.S. Pat. No. 5,231,684 issued to Narisco, et al. Other devices which are frequently used in conjunction with a light source and light delivery catheter include drug delivery devices and/or a balloon perfusion catheter (See e.g., U.S. Pat. No. 5,213,576 issued to Abiuso, et al.)

In a preferred embodiment, a non-occluding catheter can be used. Non-occluding catheters are described in a co-pending application by Kasinkas et al. entitled "Non-Occluding Light Delivery Catheter" and is incorporated herein by reference. The non-occluding catheter can be used to deliver light or UVA energy to the target region in the vessel wall while permitting blood flow through the vessel wall.

In another embodiment, the photoactivatable agent is activated externally. For example, using a monochromatic light source applied to an area of the subject's body requiring treatment, for example, the chest area. Such external light sources are well known in the art, for example, a monochromatic light source, e.g. a UV lamp.

Activation of photoactivatable agents may also be achieved by injecting a form of liquid light into the vascular system of the subject. Examples of light-emitting liquids are the bioluminescent system of firefly lucerin/lucerase and the chemiluminescent system of the Cyalume Lightstick manufactured by the American Cyanamid Company. Luciferin and luciferase are water soluble, and light is emitted when adenosine triphosphate, which is water soluble, is added to these substances. A buffer such as glycine and the metal ion, magnesium, is usually present in the solution to facilitate the reaction. Intravenous injection of these materials, obtained commercially from Sigma Chemical Company, into dogs has produced no deleterious side effects.

Aqueous peroxyoxylate chemiluminescent liquids are another example of light emitting liquids and may be injected into the bloodstream of rats and rabbits without producing any side effects. The liquid reactants typically include a triflyl oxamide and hydrogen peroxide along with sulfonated rubrene as a fluorescer and Deceresol NI as a surfactant.

A potential advantage of the use of liquid light is that all diseased vessels can be perfused with the liquid light, with one intravascular injection of the liquid light. Knowledge of the exact location of target region is unnecessary, since all would be exposed to the light.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Example
The Effect of PUVA on Blood Vessel Walls

To evaluate the effect of PUVA therapy (psoralen photoactivated with UVA light) on blood vessel walls, 17 healthy, juvenile pigs received intracoronary PUVA therapy immediately following balloon-injury. A total of 33 coronary arteries were treated and evaluated histologically twenty-eight days later.

The animals, ranging in weight from 29.8 kg to 45.4 kg, were anesthetized and prepared for treatment according to standard laboratory procedures. Quantitative coronary angiography was performed to identify suitable arterial segments for treatment and to provide baseline information. Arteries selected for study were injured using a standard coronary balloon catheter inflated three times to 120% nominal vessel size.

All animals received Uvadex (Johnson & Johnson, Exton, Penn.), an intravenous formulation of 8-methoxypsoralen, which was administered at a constant infusion rate to yield the specified dose at sixty minutes following the start of infusion. This constant infusion was maintained until light delivery was completed.

At approximately sixty minutes following the start of Uvadex infusion, the intravascular light delivery procedure was started. The light delivery system consisted of a Compass, frequency tripled YAG laser, (Coherent, Santa Clara, Calif.) optically coupled to a light guide and delivery catheter specifically designed to deliver light to coronary arteries (Illumenex Corporation, Plymouth, Minn.). The light guide, delivery catheter, and light delivery procedure are described in more detail in U.S. Pat. Nos. 5,620,438 and 5,833,682 both issued to Amplatz et al.

As shown in Table 1 below, six PUVA doses (including controls) were evaluated by varying the amount of psoralen administered to the animal and the amount of light (355 nm, 40 kHz pulsed) delivered to the artery. Although light treatment parameters vary with vessel diameter, the delivery of a 10 $J/cm^2$ dose to a 3.2 mm diameter artery typically involved 170 mW delivered for 210 seconds. Other light doses were achieved by varying the amount of power and/or light exposure time. Arteries assigned to the control received a constant infusion of Uvadex, and underwent an equivalent light delivery procedure, except that the power level was set to 0 mW.

TABLE 1

PUVA Doses

| Psoralen | UVA | Number of Arteries |
|---|---|---|
| 1.0 mg/kg | 10 $J/cm^2$ | 5 |
| 0.5 mg/kg | 10 $J/cm^2$ | 5 |
| 0.125 mg/kg | 10 $J/cm^2$ | 9 |
| 0.250 mg/kg | 1 $J/cm^2$ | 2 |
| 0.125 mg/kg | 3.3 $J/cm^2$ | 2 |
| 1.0 mg/kg | 0 $J/cm^2$ | 3 |
| 0.5 mg/kg | 0 $J/cm^2$ | 3 |
| 0.125 mg/kg | 0 $J/cm^2$ | 4 |

To determine the concentration of Uvadex in plasma, blood samples were taken at fifteen-minute intervals during and following the completion of the intravenous infusion. Additional blood samples were taken during light delivery for purposes of determining the PUVA treatment dose. Blood samples were processed and blind-labeled for analysis to determine psoralen plasma concentrations (Jefferson University Photobiology Lab, Philadelphia, Penn.) according to methods described by Gasparro et al., (1988) *J. Invest. Dermatol.* 90: 234–236.

At approximately 28 days after treatment, animals were euthanized according to standard laboratory procedures immediately following completion of quantitative coronary angiography. The hearts from each animal were perfusion fixed with formalin and the coronary arteries excised. Histological sections were prepared from the excised arteries, and morphometric data was obtained from these sections according to standard procedures.

To evaluate the effect of PUVA therapy to strengthen arterial walls, the area comprising the adventitial layer of the artery (Adventitial Area) was calculated for each of the 189 histological sections prepared from the 33 arteries enrolled in the study. An increase in adventitial area is strongly indicative of strengthening of the vessel wall.

Analysis I

To evaluate whether PUVA therapy effected the Adventitial Area, each of the 189 arterial sections was assigned to a Treatment or Control Group, and differences between the groups was assessed. As shown in Table 2 below, the average Adventitial Area for 155 arterial sections of the Treatment Group was 5.6 $mm^2$, whereas the 34 sections of the Control Group averaged only 2.7 $mm^2$. An analysis of the difference between the sample means (one-tail, 5%, assuming unequal variances) indicated that the difference, approximately 2.9 $mm^2$, was statistically significant, with a probability value (p-value) of $4.1 \times 10^{-15}$.

TABLE 2

Adventitial Area, Treatment v. Controls

|  | Treatment Group | Control Group |
|---|---|---|
| Number of Arteries | 23 | 10 |
| Number of Sections | 155 | 34 |
| Average | 5.6 | 2.7 |
| Variance | 10.9 | 1.4 |
| Sample Mean Difference | 2.9 | |
| Standard Error | 0.33229 | |
| t Statistic | 8.749 | |
| P-value | $4.1 \times 10^{-15}$ | |

Analysis 2

To evaluate whether the effect of PUVA therapy on Adventitial Area was dose-dependent, each of the 189 arterial sections was assigned to one of four Treatment Dose Groups according to criteria listed in Table 3 below. For purposes of analysis, a Treatment Dose was defined to be the product of the psoralen concentration in plasma (based on blood samples taken at the time of light delivery) and energy density (based on power measurements taken from the delivery catheter following light delivery), and is given in units of nanograms/ml×$J/cm^2$.

TABLE 3

Treatment Dose Groups

| Treatment Dose Group | Grouping Criteria |
|---|---|
| High | 5,000 < Treatment Dose |
| Medium | 1,000 < Treatment Dose <= 5,000 |
| Low | 0 < Treatment Dose <= 1,000 |
| Control | Treatment Dose = 0 |

The results from the study are summarized in Table 4 below. These results demonstrated that the average Adventitial Area increased with Treatment Dose Group, and that the differences were statistically different between all paired groups except Low and Controls.

TABLE 4

Adventitial Area by Treatment Dose Group

|  | High | Medium | Low | Control |
|---|---|---|---|---|
| Number of Arteries | 6 | 7 | 10 | 10 |
| Number of Sections | 44 | 55 | 56 | 34 |
| Average | 8.4 | 5.9 | 3.3 | 2.7 |
| Variance | 8.9 | 9.4 | 1.9 | 1.4 |
| Sample Mean Difference | 2.50 | 2.74 | 0.45 | |
| Standard Error | 0.61055 | 0.45098 | 0.27088 | |
| t Statistic | 4.098 | 6.076 | 1.649 | |
| P-value | $4.4 \times 10^{-5}$ | $2.4 \times 10^{-8}$ | 0.052 | |

Analysis 3

To further evaluate whether the effect of PUVA therapy on Adventitial Area was dose-dependent, Adventitial Area was plotted versus Treatment Dose for the 189 arterial sections, as illustrated in FIG. 1. A simple linear regression of this data indicated that there was a positive, statistically-significant relationship between the Adventitial Area and Treatment Dose. The statistical analysis data corresponding to FIG. 1 is presented in Tables 5 A–C, below.

TABLE 5A

Statistical Analysis Data
Regression Statistics

| | |
|---|---|
| Multiple R | 68.2% |
| R Square | 46.5% |
| Adjusted R Square | 46.2% |
| Standard Error | 2.37 |
| Observations | 189 |

TABLE 5B

Statistical Analysis Data
ANOVA

| | df | SS | MS | F | Significance F |
|---|---|---|---|---|---|
| Regression | 1 | 909 | 909 | 162 | $3.4 \times 10^{-27}$ |
| Residual | 187 | 1046 | 6 | | |
| Total | 188 | 1956 | | | |

TABLE 5C

Statistical Analysis Data

| Regression Parameters | Coefficients | Standard Error | t Statistic | P-value |
|---|---|---|---|---|
| Intercept | 3.2 | 0.229 | 13.9 | $1.1 \times 10^{-30}$ |
| Treatment Dose | $7.1 \times 10^{-4}$ | $5.6 \times 10^{-5}$ | 12.7 | $3.5 \times 10^{-27}$ |

Collectively, the results of this study demonstrated that (i) intracoronary PUVA therapy increased the size of the adventitial layer of the artery, and (ii) such adventitial growth was dose dependent.

What is claimed is:

1. A method for strengthening a vessel wall in an area of an aneurysm of a subject comprising:
   identifying a region of weakness in a vessel wall of an aneurysm, the region of weakness comprising at least one target layer;
   applying an agent in combination with energy to the region of weakness; and
   inducing fibrosis in a target layer, to thereby strengthen the vessel wall.

2. The method of claim 1, wherein the step of identifying the region of weakness comprises using ultrasound analysis.

3. The method of claim 1, wherein the step of identifying the region of weakness comprises using X-ray analysis.

4. The method of claim 1, wherein the step of applying energy to the region of weakness comprises irradiating the region of weakness with X-ray irradiation in an amount effective to induce fibrosis in a target layer.

5. The method of claim 1, wherein the step of applying energy to the region of weakness comprises irradiating the region of weakness with UV irradiation in an amount effective to induce fibrosis in a target layer.

6. The method of claim 1, wherein the step of applying energy to the region of weakness comprises irradiating the region of weakness with IR irradiation in an amount effective to induce fibrosis in a target layer.

7. The method of claim 1, wherein the step of applying energy to the region of weakness comprises irradiating the region of weakness with microwave irradiation in an amount effective to induce fibrosis in a target layer.

8. The method of claim 1, wherein the step of applying energy to the region of weakness comprises irradiating the region of weakness with heat irradiation in an amount effective to induce fibrosis in a target layer.

9. The method of claim 1, wherein the step of applying energy to the region of weakness comprises irradiating the region of weakness with RF irradiation in an amount effective to induce fibrosis in a target layer.

10. The method of claim 1, wherein the method further comprises, administering a therapeutically effective amount of an agent to a subject, such that the agent is taken up by at least one target layer of the vessel wall.

11. The method of claim 10, wherein the method further comprises,
    administering a therapeutically effective amount of photoactivatable agent, such that the photoactivatable agent is activated upon irradiation to induce fibrosis in a target layer.

12. A method of strengthening a vessel wall having an adventitial area in an area of an aneurysm of a subject comprising:
    administering a therapeutically effective amount of a photoactivatable agent to a subject, such that the agent is taken up by at least one layer of the vessel wall of the aneurysm;
    applying energy to a target region of the vessel wall in an area of the aneurysm, such that the photoactivatable agent is activated to strengthen the vessel wall; and
    increasing an adventitial area of the vessel wall.

13. The method of claim 12, wherein the step of administering a therapeutically effective amount of a photoactivatable agent further comprises systemically administering the photoactivatable agent.

14. The method of claim 12, wherein the step of administering a therapeutically effective amount of a photoactivatable agent further comprises locally administering the photoactivatable agent.

15. The method of claim 12, wherein the step of administering a therapeutically effective amount of a photoactivatable agent further comprises administering a psoralen agent or derivatives thereof.

16. The method of claim 12, wherein the step of applying energy to a target region further comprises irradiating the target region internally using a light delivery catheter.

17. The method of claim 16, wherein the step of applying energy to a target region further comprises irradiating the target region using a light delivery catheter without occluding fluid flow.

18. The method of claim 12, wherein the step of applying energy to a target region further comprises irradiating the target region externally using an external light delivery source.

19. The method of claim 12, wherein the step of applying energy to a target region further comprises irradiating the target region with UV irradiation.

20. A method for increasing an adventitial area of a blood vessel wall in an area of an aneurysm comprising:
   recognizing that increasing an adventitial area of a blood vessel strengthens the blood vessel;
   administering a therapeutically effective amount of a photoactivatable agent to a subject, such that the agent is taken up by the adventitial area of the vessel in an area of the aneurysm;
   applying energy to a target region of the blood vessel wall so that the photoactivatable agent is activated; and
   increasing the adventitial area of the vessel in an area of the aneurysm.

21. The method of claim 20, wherein the step of administering a therapeutically effective amount of a photoactivatable agent further comprises systemically administering the photoactivatable agent.

22. The method of claim 21, wherein the step of administering a therapeutically effective amount of a photoactivatable agent further comprises locally administering the photoactivatable agent.

23. The method of claim 21, wherein the step of administering a therapeutically effective amount of a photoactivatable agent further comprises administering a psoralen agent or derivatives thereof.

24. The method of claim 21, wherein the step of applying energy to a target region further comprises irradiating the target region internally using a light delivery catheter.

25. The method of claim 24, wherein the step of applying energy to a target region further comprises irradiating the target region using a light delivery catheter without occluding fluid flow.

26. The method of claim 21, wherein the step of applying energy to a target region further comprises irradiating the target region externally using an external light delivery source.

27. The method of claim 21, wherein the step of applying energy to a target region further comprises irradiating the target region with UV irradiation.

28. A method for treating an aneurysm by increasing an adventitial area of a blood vessel in an area of an aneurysm comprising:
   administering a therapeutically effective amount of a photoactivatable agent to a subject, such that the agent is taken up by an adventitial area of the blood vessel in an area of the aneurysm;
   applying energy to the site of the aneurysm to react within the photoactivatable agent; and
   increasing an adventitial area in the area of the aneurysm.

29. The method of claim 1, wherein the step of administering a therapeutically effective amount of photoactivatable agent further comprises systemically administering the photoactivatable agent.

30. The method of claim 1, wherein the step of administering a therapeutically effective amount of photoactivatable agent further comprises locally administering the photoactivatable agent.

31. The method of claim 1, wherein the step of administering a therapeutically effective amount of photoactivatable agent further comprises administering a psoralen agent or derivatives thereof.

32. The method of claim 30, wherein the step of applying energy to the site of the aneurysm further comprises irradiating the site of the aneurysm internally using a light delivery catheter.

33. The method of claim 32, wherein the step of applying energy to the site of the aneurysm further comprises irradiating the site of the aneurysm internally using a light delivery catheter without occluding fluid flow.

34. The method of claim 30, wherein the step of applying energy to the site of the aneurysm further comprises irradiating the site of the aneurysm externally using an external light delivery source.

35. The method of claim 30, wherein the step of applying energy to the site of the aneurysm further comprises irradiating the site of the aneurysm with UV irradiation.

36. A method for strengthening a vessel wall in an area of an aneurysm of a subject comprising,
   irradiating a target region with UVC irradiation; and
   inducing fibrosis in at least one layer of the vessel wall in the area of the aneurysm.

37. The method of claim 36, wherein the step of irradiating the target region further comprises irradiating the target region internally using a light delivery catheter.

38. The method of claim 37, wherein the step of irradiating the target region further comprises irradiating the target region internally using a light delivery catheter without occluding fluid flow.

39. The method of claim 36, wherein the step of irradiating the target region further comprises irradiating the target region externally using an external light delivery source.

40. The method of claim 36, wherein the step of irradiating the target region further comprises irradiating the target region with UVC irradiation having a wavelength of about 240 to 370 nanometers.

41. A method for increasing an adventitial area of a blood vessel wall in an area of an aneurysm comprising,
   irradiating the target region with UVC irradiation; and
   increasing an adventitial area of the blood vessel wall in the area of the aneurysm.

42. The method of claim 41, wherein the step of irradiating the target region further comprises irradiating the target region internally using a light delivery catheter.

43. The method of claim 42, wherein the step of irradiating the target region further comprises irradiating the target region internally using a light delivery catheter without occluding fluid flow.

44. The method of claim 41, wherein the step of irradiating the target region further comprises irradiating the target region externally using an external light delivery source.

45. The method of claim 41, wherein the step of irradiating the target region further comprises irradiating the target region with UVC irradiation having a wavelength of about 240 to 370 nanometers.

46. A method for treating an aneurysm by increasing an adventitial area of a blood vessel in an area of an aneurysm comprising,
   irradiating the site of the aneurysm with UVC irradiation; and
   increasing an adventitial area in the area of the aneurysm.

47. The method of claim 46, wherein the step of irradiating the site of the aneurysm further comprises irradiating the site of the aneurysm internally using a light delivery catheter.

48. The method of claim 47, wherein the step of irradiating the site of the aneurysm further comprises irradiating the site of the aneurysm internally using a light delivery catheter without occluding the fluid flow.

49. The method of claim 46, wherein the step of irradiating the site of the aneurysm further comprises irradiating the site of the aneurysm externally using an external light delivery source.

50. The method of claim 46, wherein the step of irradiating the site of the aneurysm further comprises irradiating the site of the aneurysm with UVC irradiation having a wavelength of about 240 to 370 nanometers.

* * * * *

UNITED STATES PATENT AND TRADEMARK OFFICE
CERTIFICATE OF CORRECTION

PATENT NO. : 6,719,778 B1
DATED : April 13, 2004
INVENTOR(S) : Robert A. Van Tassel and Michael Kasinkas It is certified that error appears in the above-identified patent and that said Letters Patent is hereby corrected as shown below:

Column 7,
Line 27, change "used to treat an lesion" to -- used to treat a lesion --

Column 12,
Lines 18 and 19, change "Treatment Group was 5.6 mm$^2$" to -- Treatment Group was 5.6mm$^2$, --

Column 15,
Lines 56, 60 and 64, change "The method of claim 1" to -- The method of claim 28 --

Column 16,
Line 1, change "The method of claim 30" to -- The method of claim 28 --

Signed and Sealed this

Eighteenth Day of January, 2005

JON W. DUDAS
*Director of the United States Patent and Trademark Office*